United States Patent
Remon

(10) Patent No.: US 11,224,558 B2
(45) Date of Patent: Jan. 18, 2022

(54) XANTHOHUMOL-BASED COMPOSITIONS

(71) Applicant: Jean Paul Remon, Melle (BE)

(72) Inventor: Jean Paul Remon, Melle (BE)

( * ) Notice: Subject to any disclaimer, the term of this patent is extended or adjusted under 35 U.S.C. 154(b) by 26 days.

(21) Appl. No.: 16/604,245

(22) PCT Filed: Apr. 12, 2018

(86) PCT No.: PCT/EP2018/059423
§ 371 (c)(1),
(2) Date: Oct. 10, 2019

(87) PCT Pub. No.: WO2018/189311
PCT Pub. Date: Oct. 18, 2018

(65) Prior Publication Data
US 2020/0155425 A1 May 21, 2020

(30) Foreign Application Priority Data

Apr. 13, 2017 (EP) .................................. 17166458

(51) Int. Cl.
*A61K 8/02* (2006.01)
*A23L 33/00* (2016.01)
*A61K 8/04* (2006.01)
*A61K 8/06* (2006.01)
*A61K 8/35* (2006.01)
*A61K 8/81* (2006.01)
*A61K 9/00* (2006.01)
*A61K 9/08* (2006.01)
*A61K 9/14* (2006.01)
*A61K 9/20* (2006.01)
*A61K 9/48* (2006.01)
*A61K 31/12* (2006.01)
*A61K 31/79* (2006.01)

(52) U.S. Cl.
CPC .......... *A61K 8/0225* (2013.01); *A23L 33/30* (2016.08); *A61K 8/042* (2013.01); *A61K 8/06* (2013.01); *A61K 8/35* (2013.01); *A61K 8/8182* (2013.01); *A61K 9/0056* (2013.01); *A61K 9/0095* (2013.01); *A61K 9/08* (2013.01); *A61K 9/14* (2013.01); *A61K 9/20* (2013.01); *A61K 9/4808* (2013.01); *A61K 31/12* (2013.01); *A61K 31/79* (2013.01); *A61K 2800/612* (2013.01); *A61K 2800/80* (2013.01)

(58) Field of Classification Search
None
See application file for complete search history.

(56) References Cited

U.S. PATENT DOCUMENTS

| 9,006,293 | B2 | 4/2015 | Yamaguchi et al. | |
|---|---|---|---|---|
| 2009/0209654 | A1* | 8/2009 | Kuhrts | A61P 9/00 514/685 |
| 2009/0258094 | A1 | 10/2009 | Ono et al. | |
| 2011/0207697 | A1 | 8/2011 | Ono et al. | |
| 2012/0201865 | A1* | 8/2012 | Dorairaju | A61K 9/1641 424/400 |

FOREIGN PATENT DOCUMENTS

| DE | 102005035864 A1 | 2/2007 |
|---|---|---|
| WO | 2003003997 A2 | 1/2003 |
| WO | 2010044076 A2 | 4/2010 |

OTHER PUBLICATIONS

Kollidon VA64 Product Information (accessed from https://pharmaceutical.basf.com/global/en/drug-formulation/products/kollidon-va64.html).*
Ozguney et al., "Development and characterization of extended release Kollidon(R) SR mini-matrices prepared by hot-melt extrusion", European Journal of Pharmaceutics and Biopharmaceutics, vol. 73, No. 1, pp. 140-145, Sep. 1, 2009.
Maschke et al., "Effect of Preparation Method on Release Behavior of Kollidon SR Tablets Hot Melt Extrusion versus Direct Compression References", 36th Annual Meeting and Exposition of the Controlled Release Society Compression Behavior of Kollidon Sr., Proceedings 4th World Meeting on Pharmaceutics, Biopharmaceutics and Pharmaceutical Technology, vol. 1, Jul. 22, 2009.
Crowley et al., "Hot Melt Extrusion of Amorphous Solid Dispersions", Internet Citation, XP002773166, Jan. 1, 2015.
Search Report and Written Opinion pertaining to Application No. PCT/EP2018/059423 dated Jun. 4, 2018.
European Search Report pertaining to Application No. 17166458.4 dated Oct. 19, 2017.

* cited by examiner

*Primary Examiner* — Robert A Wax
*Assistant Examiner* — Randeep Singh
(74) *Attorney, Agent, or Firm* — Dinsmore & Shohl, LLP

(57) ABSTRACT

This invention relates to xanthohumol-based compositions, yielded in a hot-melt extrusion process (HME) using one or more water-soluble nutritionally and/or cosmetically acceptable thermoplastic polymers, such as selected from hydroxypropylmethyl-cellulose (HPMC), a vinylpyrrolidone-vinyl acetate copolymer, and combinations thereof. The present invention also relates to topical and oral formulations comprising such extruded xanthohumol-based compositions, as well as the use of one or more water-soluble nutritionally and/or cosmetically acceptable thermoplastic polymers in a hot-melt extrusion process of xanthohumol.

15 Claims, No Drawings

XANTHOHUMOL-BASED COMPOSITIONS

FIELD OF THE INVENTION

This invention relates to xanthohumol-based compositions, yielded in a hot-melt extrusion process (HME) using one or more water-soluble nutritionally and/or cosmetically acceptable thermoplastic polymers, such as selected from hydroxypropylmethylcellulose (HPMC), a vinylpyrrolidone-vinyl acetate copolymer, and combinations thereof. The present invention also relates to topical and oral formulations comprising such extruded xanthohumol-based compositions, as well as the use of one or more water-soluble nutritionally and/or cosmetically acceptable thermoplastic polymers in a hot-melt extrusion process of xanthohumol.

BACKGROUND TO THE INVENTION

Xanthohumol is a bioflavonoid derived from hops, more specifically the female hop plant. Xanthohumol exhibits a broad range of bioactivities, but is especially renowned for its anti-oxidant activity. Thereto, it is considered useful in the treatment of diseases associated with oxidative stress such as for example cancer, diabetes and dyslipidaemia.

Due its anti-oxidant activity, it is of course also an interesting component in cosmetic compositions. However, given the fact that xanthohumol has a low water-solubility, it is difficult to include it in such formulations. Furthermore, attempts to increase the water-solubility of xanthohumol by e.g. heating, result in conversion of xanthohumol into isoxanthumol, which is undesired. Therefore, until now, it has been very difficult to formulate xanthohumol in a cosmetic watery composition.

Current xanthohumol-containing products have at least two disadvantages. First, the bioavailability of xanthohumol in these products is very poor due to its low water-solubility. Second, xanthohumol products often contain a substantial amount of isoxanthohumol, which results from the breakdown of xanthohumol during preparation (e.g. in heating steps) or storage of xanthohumol-containing products. The presence of isoxanthohumol is disadvantageous because it possesses undesirable estrogenic activity. Thus, there is a need to develop new formulations that contain high amounts of bioavailable xanthohumol and little or no isoxanthohumol.

Xanthohumol compositions for cosmetic purposes are already known in the prior art. US20110207697 for instance discloses a composition for treating skin diseases, comprising a xanthohumol/cyclodextrin complex in a pharmaceutically acceptable excipient. Other compositions are disclosed in e.g. DE102005035864, WO2010044076, U.S. Pat. No. 9,006,293 and WO2003003997.

It was surprisingly found that hot-melt extrusion of xanthohumol in the presence of a water-soluble nutritionally and/or cosmetically acceptable thermoplastic polymers such as for example hydroxypropylmethylcellulose (HPMC) or a vinylpyrrolidone-vinyl acetate copolymer, followed by milling resulted in a powder suitable for use in water-containing formulations. Although heating is used during the hot-melt extrusion process, it was found that little or no conversion into isoxanthohumol occurred, and that the selection of thermoplastic polymers thus appears to protect xanthohumol from being converted into isoxanthohumol.

SUMMARY OF THE INVENTION

The current invention describes a composition comprising xanthohumol and one or more water-soluble nutritionally and/or cosmetically acceptable thermoplastic polymers selected from hydroxypropylmethylcellulose (HPMC) and a vinylpyrrolidone-vinyl acetate copolymer; wherein said composition is in the form of an extrudate; specifically a hot-melt extrudate.

In a certain embodiment, the hot-melt extruded composition comprises between 1% and 50% xanthohumol; in particular between 10% and 30% xanthohumol.

In another embodiment, said composition is formulated in the form of a powder, a nanoparticulate form or a microparticulate form.

In a certain embodiment, the present invention provides a topical cosmetic formulation comprising the composition as defined herein.

In a particular embodiment, this topical cosmetic formulation is in the form of a gel, cream, foam, paste, lotion, milk, emulsion, solution, suspension, ointment, lipstick, shower gel, bath gel, shampoo, sunscreen, after sun preparation, spray, moisturizer, anti-dandruff formulation, antiperspirant or deodorant composition.

In another particular embodiment, the topical cosmetic formulation of the present invention further comprises one or more components selected from the list comprising: hydration agents, vitamins, antioxidants, peptides, plant extracts, anti-slimming components, anti-ageing components, anti-acne components, anti-inflammatory components.

In a certain embodiment, the present invention provides an oral formulation comprising the composition as defined herein.

In a specific embodiment, the oral formulation of the present invention is in the form of a pharmaceutical formulation, a nutraceutical formulation or a food supplement.

In a more specific embodiment, the oral formulation of the present invention is in the form of a powder, capsule, tablet, pill, lozenge, sachet, cachet, elixir, suspension, emulsion, solution, syrup, soft and hard gelatin capsules, granule or pellet.

The present invention also provides the compositions and formulations according to the present invention for use in human and/or veterinary medicine; or alternatively in cosmetics.

Furthermore, the current invention provides a method for the preparation of a composition as defined herein; said method comprising the steps of:

mixing xanthohumol, with one or more water-soluble nutritionally and/or cosmetically acceptable thermoplastic polymers selected from the list comprising hydroxypropylmethylcellulose (HPMC) and vinylpyrrolidine-vinyl acetate copolymer;

hot-melt extruding said mixture; and optionally milling said hot-melt extruded mixture.

In a further aspect, the present invention provides the use of one or more water-soluble nutritionally and/or cosmetically acceptable thermoplastic polymers selected from the list comprising hydroxypropylmethylcellulose (HPMC) and vinylpyrrolidine-vinyl acetate copolymer; in a hot-melt extrusion process of xanthohumol.

DETAILED DESCRIPTION OF THE INVENTION

As already defined herein above, the current invention provides a composition comprising xanthohumol and one or more water-soluble nutritionally and/or cosmetically acceptable thermoplastic polymers selected from hydroxypropylmethylcellulose (HPMC) and a vinylpyrrolidone-vinyl acetate copolymer; wherein said composition is in the form of an extrudate; specifically a hot-melt extrudate.

In the context of the present invention the term "xanthohumol" is to be understood as meaning a prenylated chalconoid obtainable from hop and beer, and is represented by the following formula:

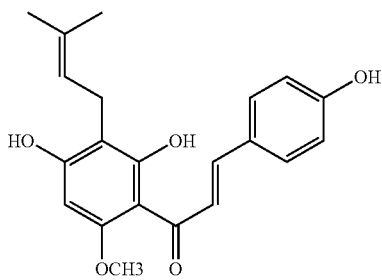 [SMILES: COc1cc(O)c(CC=C(C)C)c(O)c1C(=O)/C=C/c1ccc(O)cc1]

Xanthohumol as used in the present invention may be a commercially available pure form of the molecule, or alternatively be an (enriched) extract obtained from a suitable source such as hop.

In the context of the present invention the term "isoxanthohumol" is to be understood as the corresponding prenylated flavanone of xanthohumol, and is represented by the following formula:

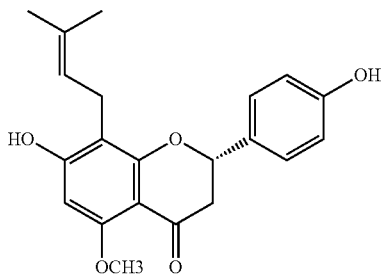 [SMILES: COc1cc(O)c(CC=C(C)C)c2c1C(=O)C[C@@H](c1ccc(O)cc1)O2]

Isoxanthohumol can be obtained from conversion of xanthohumol such as by heating. However, isoxanthohumol is undesired for human use, since it is a phytoestrogen in contrast to xanthohumol.

The compositions of the present invention are made using an extrusion process, which in general comprises at least 2 steps including dry mixing and extrusion. First, the materials are dry mixed to achieve a homogeneous powder. The blend is hot-melt extruded to form rod-shaped particles of uniform diameter that may subsequently be milled or reduced in size by any other means. Where applicable, the extrudates or size-reduced particles obtained therefrom are used in the formulations of the present invention. The resulting end products of such an extrusion process (prior to size-reduction) according to the present invention, are termed 'extrudates'. Hence, the compositions of the present invention are characterized in being in the form of an extrudate, i.e. by being produced using the described extrusion process.

As already detailed herein above, it was surprisingly found that a thermoplastic polymer could significantly reduce conversion of xanthohumol to isoxanthohumol in a hot-melt extrusion process. Such thermoplastic polymer is preferably nutritionally and/or cosmetically acceptable, depending on the type of formulation to be used in, e.g. nutritionally acceptable for oral formulations, cosmetically acceptable for topical formulations. More specifically, such thermoplastic polymers are preferably "GRAS" (Generally Recognized/Regarded As Safe) components. Generally recognized as safe (GRAS) is an American Food and Drug Administration (FDA) designation that a chemical or substance added to food is considered safe by experts, and so is exempted from the usual Federal Food, Drug, and Cosmetic Act (FFDCA) food additive tolerance requirements.

In the context of the present invention, the term "thermoplastic material" is meant to be a material which is pliable or moldable above a specific temperature and which becomes solid again upon cooling. Such thermoplastic materials are in particular highly suitable for use in a hot-melt extrusion process as used in the current invention.

Suitable thermoplastic polymers within the context of the invention may for example be selected from the list comprising homopolymers and copolymers of N-vinyl lactams, cellulose derivatives, high molecular polyalkylene oxides, polyvinyl alcohol-polyethylene glycol-graft copolymers, graft copolymers comprising a poly(alkylene glycol) backbone and a vinyl acetate/N-vinylcaprolactam copolymer grafted onto the backbone, polyacrylates and polymethacrylates, polyacrylamides, vinyl acetate polymers, polyvinyl alcohol, oligo- and polysaccharides, polyhydroxyalkanoates, polyamino acids, proteins and polypeptides and mixtures thereof. In particular, the thermoplastic polymers may be selected from the list comprising hydroxypropylmethylcellulose (HPMC), a vinylpyrrolidone-vinyl acetate copolymer, Eudragit E and mixtures thereof. More in particular, the thermoplastic polymer of the present invention may be hydroxypropylmethylcellulose (HPMC), a vinylpyrrolidone-vinyl acetate copolymer, or a combination thereof.

HPMC as used in the current invention is meant to be hydroxypropylmethylcellulose or hypromellose and is represented by the following general formula:

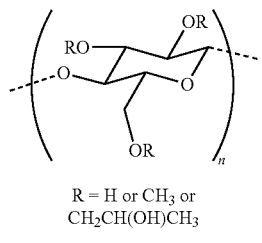

R = H or CH$_3$ or CH$_2$CH(OH)CH$_3$

Vinylpyrrolidone-vinyl acetate copolymer as used herein is meant to be a copolymer of (poly)vinylpyrrolidone (PVP) and vinyl acetate (VA), each represented by the appropriate general formula:

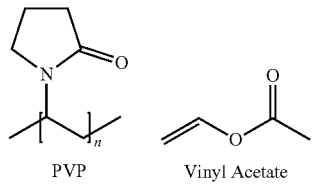

PVP     Vinyl Acetate

Both components may be combined to a co-polymer using any suitable ratio. In that respect several different combinations are marketed for example under the tradename Kollidon®. A particularly suitable combination within the context of the present invention is Kollidon® VA64, which is a copovidone having the CAS registration N° 25086-89-9. It is defined as being a vinylpyrrolidone-vinyl acetate copolymer in a ratio of 6:4 by mass and represented by the following general formula:

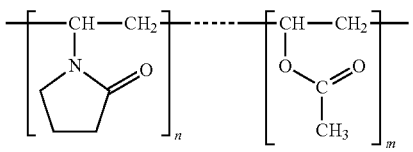

In a certain embodiment, the composition of the present invention comprises between 1% and 50% xanthohumol; in particular between 10% and 30% xanthohumol. More in particular, the composition of the present invention comprises about 1%, 2%, 3%, 4%, 5%, 6%, 7%, 8%, 9%, 10%, 15%, 20%, 25%, or 30% of xanthohumol.

In another particular embodiment, the composition of the present invention comprises between 50% and 90% of the thermoplastic polymer; in particular between 70% and 90% of the thermoplastic polymer. More in particular, the composition of the present invention comprises about 90%, 85%, 80%, 75%, or 70% of the thermoplastic polymer.

Depending on the type and concentration of thermoplastic polymer used, the composition of the present invention may further comprise a plasticizer and/or a tensio-active agent. Whenever a plasticizer is present it is usually present at a concentration of between 1% and 30% with respect to the polymer, more in particular between 10% and 30%, such as 15%, 20%, 25% or 30%. Whenever a tensio-active agent is present, it is usually present at a maximum concentration of 20% of the total composition, such as 15%, 10%, 5%, 4%, 3%, 2%, 1%.

In another embodiment, the composition is formulated in the form of a powder, a nanoparticulate form or a microparticulate form. Such forms of the composition may be obtained for example by milling the extrudates to obtain the desired particle size. However, any other method suitable for obtaining such forms from the extrudates may be used.

As used herein, the term "powder" is meant to be a solid substance which is reduced to a state of fine, loose particles (i.e. multiparticulate) such as for example by crushing, grinding or milling. As used herein, "multiparticulate" means a plurality of discrete, or aggregated, particles, pellets, beads, granules or mixture thereof irrespective of their size, shape or morphology. By way of example each particle may have a diameter of from about 0.1 mm to about 5.0 mm, e.g. from about 0.5 mm to about 5.0 mm, in particular from about 0.5 mm to about 2.5 mm, more particularly from about 0.5 mm to about 1.0 mm, more in particular about 0.75 mm. The average size of the individual powder particles (i.e. multiparticulate) determines its eventual nomenclature. For example, "nanoparticulate" refers to a multiparticulate in which the effective average particle size of the particles therein is less than 1 nm in diameter. On the other hand, "microparticulate" refers to a multiparticulate in which the effective average particle size of the particles therein is between 1 μm and 1 nm in diameter.

In a certain embodiment, the present invention provides a topical cosmetic formulation comprising the composition as defined herein. Thereto, the extrudates are further processed to a format suitable for incorporation in a cosmetic formulation. For example, the extrudates may be milled to a powder, which can then be included in a standard or custom-made cosmetic formulation, such as for example in a gel, cream, foam, paste, lotion, milk, emulsion, solution, suspension, ointment, lipstick, shower gel, bath gel, shampoo, sunscreen, after sun preparation, spray, moisturizer, anti-dandruff formulation, antiperspirant or deodorant composition. Evidently, any other form of cosmetic formulation which allows the inclusion of the extrudates or further processed forms derived thereof, are also envisaged within the context of the current invention.

In another particular embodiment, this topical cosmetic formulation further may comprise one or more additional components such as selected from the list comprising: hydration agents, vitamins, antioxidants, peptides, plant extracts, anti-slimming components, anti-ageing components, anti-acne components, anti-inflammatory components.

Examples of topical formulations are shown in example 1 (day cream for persons having an age above 50 years), example 2 (day cream for persons having an age below 50 years), example 3 (handcream), example 4 (anti-Cellulitis Cream), and example 5 (anti-Acne Cream comprising different combinations of xanthohumol extrudate with Cetostearylalcohol, Retinolpalmitate, Ceteareth 20, Isopropylpalmitate, Triglyceride mixture, Aloe extract, White wax, Vaseline, Cremophor WO7, Tocoferolacetate, Nicotinamide, Lactic acid, Hamamelis extract, Kleptose, Potassium sorbate, Carbopol 980, Glycerine, NaOH and/or $H_2O$.

While the invention is in particular suitable for formulating xanthohumol in watery cosmetic formulations, it may also be suitably used in the formulation of xanthohumol in formulations for oral use. Thereto, the present invention also provides an oral formulation comprises the compositions as described herein. Such oral formulation may for example be in the form of a pharmaceutical formulation, a nutraceutical formulation or a food supplement.

Pharmaceutical formulations as used herein are formulations including the compositions of the invention in combination with other pharmaceutically acceptable compounds such as excipients, carriers, . . . .

Nutraceutical formulations as used herein are formulations that include the compositions of the invention in combination with natural ingredients and/or supplements that promote good health.

Food supplement as used herein contain the compositions of the invention in an edible carrier (food product). Examples of an edible carrier include starch, cyclodextrin, maltodextrin, methylcellulose, carboxymethoxycellulose, xanthan gum, and aqueous solutions thereof. Such food products can be prepared by methods well known in the food industry. As used herein, the term "food" broadly refers to any kinds of liquid and solid/semi-solid materials that are used for nourishing humans and animals.

In a more specific embodiment, this oral formulation is in the form of a powder, capsule, tablet, pill, lozenge, sachet, cachet, elixir, suspension, emulsion, solution, syrup, soft and hard gelatin capsules, granule and pellet.

The present invention also provides the compositions and formulations according to the present invention for use in human and/or veterinary medicine; or alternatively in cosmetics.

Furthermore, the current invention provides a method for the preparation of a composition as defined herein; said method comprising the steps of:
   mixing xanthohumol, with one or more water-soluble nutritionally and/or cosmetically acceptable thermoplastic polymers;
   hot-melt extruding said mixture; and
   optionally milling said hot-melt extruded mixture.

In a particular embodiment, the method according to the present invention comprises the steps of
- mixing xanthohumol, with one or more water-soluble nutritionally and/or cosmetically acceptable thermoplastic polymers selected from the list comprising hydroxypropylmethylcellulose (HPMC) and vinylpyrrolidine-vinyl acetate copolymer;
- hot-melt extruding said mixture; and
- optionally milling said hot-melt extruded mixture.

Where in the context of this invention, a method is defined, the steps as mentioned therein are preferably performed in the listed order.

In a final aspect, the present invention provides the use of one or more water-soluble nutritionally and/or cosmetically acceptable thermoplastic polymers in a hot-melt extrusion process of xanthohumol is disclosed. In a specific embodiment, the present invention provides the use of hydroxypropylmethylcellulose (HPMC) and/or vinylpyrrolidine-vinyl acetate copolymer; in a hot-melt extrusion process of xanthohumol.

EXAMPLES

The invention will now be illustrated by means of the following exemplary compositions, which do not limit the scope of the invention in any way.

Materials and Methods

Preparation of Xanthohumol Extrudates

The xanthohumol extrudates were prepared using the following general process: A mixture of Kollidon VA64 and Xanthohumol (90:10) was hot melt extruded using a co-rotating twin extruder at a screw speed of 90 rmp at 140° C. The thermoplastic extrudate was collected, cooled to room temperature and milled to obtain a powder, which was then used as such in the below mentioned formulations.

Preparation of Cosmetic Compositions

The below-mentioned compositions were made using standard protocols for making cosmetic creams:

Example 1

Composition for a Day Cream for Persons Having an Age Above 50 Years

| Composition | Amount (g) |
| --- | --- |
| Cetostearylalcohol | 20.0 |
| Ceteareth 20 ® | 7.5 |
| Isopropylpalmitate | 15.0 |
| Triglyceride mixture | 5.0 |
| Aloe extract | 0.125 |
| Tocoferolacetate | 5.0 |
| Nicotinamide | 5.0 |
| Potassium sorbate | 1.35 |
| Carbopol 980 ® | 0.75 |
| NaOH (1M) | 2.5 |
| Xanthohumol extrudate 10% | 1.0 |
| Water | 436.775 |

Example 2

Composition for a Day Cream for Persons Having an Age Below 50 Years

| Composition | Amount (g) |
| --- | --- |
| Cetostearylalcohol | 20.0 |
| Ceteareth 20 ® | 7.5 |
| Isopropylpalmitate | 15.0 |
| Triglyceride mixture | 5.0 |
| Aloe extract | 0.125 |
| Tocoferolacetate | 5.0 |
| Nicotinamide | 5.0 |
| Potassium sorbate | 1.35 |
| Carbopol 980 ® | 0.75 |
| NaOH (1M) | 2.5 |
| Xanthohumol extrudate 10% | 0.25 |
| Water | 437.525 |

Example 3

Composition For a Hand Cream

| Composition | Amount (g) |
| --- | --- |
| Cetostearylalcohol | 25.0 |
| Ceteareth 20 | 10.0 |
| Triglyceride mixture | 5.0 |
| Cremophor WO7 | 4.0 |
| Glycerine | 5.0 |
| Lactic acid | 5.0 |
| Nicotinamide | 5.0 |
| Vaseline | 10.0 |
| Hamamelis extract | 1.5 |
| Kleptose | 4.0 |
| Potassium sorbate | 1.35 |
| Xanthohumol extrudate 10% | 0.25 |
| Water | 423.9 |

Example 4

Anti-Cellulitis Cream

| Composition | Amount (g) |
| --- | --- |
| Cetostearylalcohol | 20.0 |
| Ceteareth 20 | 7.5 |
| Isopropylpalmitate | 15.0 |
| Triglyceride mixture | 5.0 |
| Coffeine | 10.0 |
| Gluconolactone | 5.0 |
| Retinolpalmitate | 0.15 |
| Xanthohumol extrudate (10%) | 1.0 |
| Potassium sorbate | 1.35 |
| Carbopol 980 | 1.25 |
| Sodium hydroxide 1M | 2.5 |
| Water | 431.25 |

Example 5

Anti-Acne Cream

| Composition | Amount (g) |
| --- | --- |
| Cetostearylalcohol | 20.0 |
| Ceteareth 20 | 7.5 |
| Isopropylpalmitate | 15.0 |
| Triglyceride mixture | 5.0 |
| Carbopol 980 | 0.75 |
| Tocoferolacetate | 5.0 |
| Nicotinamide | 5.0 |
| Potassium sorbate | 1.35 |
| Xanthohumol extrudate (10%) | 0.15 |
| Hop acid extrudate | 0.030 |
| Sodium hydroxide 1M | 2.5 |
| Water | 437.72 |

Preparations for Therapeutic Uses or Supplements

Example 6

Soluble Powder for Drinking Water Medication

| Composition | Amount (g) |
| --- | --- |
| Xanthohumol extrudate (10%) | 13.3 |
| Hop acid extrudate | 10.0 |
| Colloidal silicium dioxide | 0.5 |
| Mannitol or maltodextrine | 26.2 |

Example 7

Tablet Formulation

For a Tablet of 500 mg, Prepared Via Direct Compression

| Composition | Amount (mg) |
| --- | --- |
| Xanthohumol extrudate (10%) | 71.4 |
| Microcrystalline cellulose | 397.6 |
| Colloidal silicium dioxide | 1.0 |
| Sodium stearyl fumarate | 5.0 |
| Cross-linked polyvinylpyrrolidine | 25.0 |

Example 8: Effect of Extrusion on Isoxanthohumol Content

A mixture of Kollidon VA64 and Xanthohumol (90:10) was hot melt extruded using a co-rotating twin extruder at a screw speed of 90 rmp at 140° C. The thermoplastic extrudate was collected, cooled to room temperature and milled to obtain a powder, which was then used as such in the below mentioned formulations.

Xanthohumol and isoxanthohumol concentrations were determined before and after extrusion by a validated HPLC method. The xanthohumol versus isoxanthohumol ratio changed from 79.1 before to 197.3 after extrusion. These data clearly indicate that an extrusion process in the presence of a thermoplastic polymer significantly reduces conversion of xanthohumol into isoxanthohumol.

The invention claimed is:

1. A composition comprising from 1% to 15% by weight xanthohumol based on the total weight of the composition, and a vinylpyrrolidone-vinyl acetate copolymer; wherein the composition is in the form of a hot-melt extrudate.

2. The composition according to claim 1, wherein the extrudate is in the form of a powder, a nanoparticulate, or a microparticulate.

3. The composition according to claim 1, comprising from 10% to 15% by weight xanthohumol, based on the total weight of the composition.

4. A topical cosmetic formulation comprising the composition according to claim 1.

5. The topical cosmetic formulation according to claim 4, wherein the formulation is in the form of a gel, cream, foam, paste, lotion, milk, emulsion, solution, suspension, or ointment.

6. The topical cosmetic formulation according to claim 4, wherein the formulation further comprises one or more components chosen from vitamins, antioxidants, peptides, or plant extracts.

7. The topical cosmetic formulation according to claim 5, wherein the formulation is in the form of a lipstick, shower gel, bath gel, shampoo, sunscreen, after sun preparation, spray, moisturizer, anti-dandruff formulation, antiperspirant, or deodorant composition.

8. An oral formulation comprising the composition according to claim 1.

9. The oral formulation as defined in claim 8, which is in the form of a pharmaceutical formulation, a nutraceutical formulation or a food supplement.

10. The oral formulation according to claim 8, wherein the formulation is in the form of a powder, capsule, tablet, pill, lozenge, sachet, cachet, elixir, suspension, emulsion, solution, syrup, granule, or pellet.

11. The oral formulation according to claim 10, wherein the capsule is in the form of a soft gelatin capsule or a hard gelatin capsule.

12. A composition consisting of xanthohumol and a vinylpyrrolidone-vinyl acetate copolymer, wherein the composition is in the form of a hot-melt extrudate.

13. The composition of claim 12, consisting of:
   1% to 15% by weight xanthohumol, based on the total weight of the composition; and
   a vinylpyrrolidone-vinyl acetate copolymer.

14. The composition of claim 12, consisting of:
   10% to 15% by weight xanthohumol, based on the total weight of the composition; and
   a vinylpyrrolidone-vinyl acetate copolymer.

15. A method for the preparation of a composition according to claim 1, the method comprising:
   mixing the xanthohumol with the vinylpyrrolidine-vinyl acetate copolymer to form a mixture;
   hot-melt extruding the mixture to form a hot-melt extruded mixture; and
   optionally milling the hot-melt extruded mixture.

* * * * *